United States Patent
Liu et al.

(10) Patent No.: US 10,426,868 B2
(45) Date of Patent: Oct. 1, 2019

(54) METHOD FOR PREPARING AN ANIMAL DECELLULARIZED TISSUE MATRIX MATERIAL AND A DECELLULARIZED TISSUE MATRIX MATERIAL PREPARED THEREBY

(71) Applicant: Beijing Ruijian Gaoke Biotechnology Co., Ltd., Beijing (CN)

(72) Inventors: Zhi-gang Liu, Beijing (CN); Xinhua Liu, Beijing (CN)

(73) Assignee: Beijing Ruijian Gaoke Biotechnology Co., Ltd., Beijing (CN)

( * ) Notice: Subject to any disclaimer, the term of this patent is extended or adjusted under 35 U.S.C. 154(b) by 102 days.

(21) Appl. No.: 14/914,283

(22) PCT Filed: May 29, 2014

(86) PCT No.: PCT/CN2014/078737
§ 371 (c)(1),
(2) Date: Feb. 25, 2016

(87) PCT Pub. No.: WO2015/027727
PCT Pub. Date: Mar. 5, 2015

(65) Prior Publication Data
US 2016/0199540 A1     Jul. 14, 2016

(30) Foreign Application Priority Data
Aug. 26, 2013   (CN) .......................... 2013 1 0376619

(51) Int. Cl.
A61L 27/36     (2006.01)

(52) U.S. Cl.
CPC ......... *A61L 27/362* (2013.01); *A61L 27/3683* (2013.01); *A61L 27/3687* (2013.01); *A61L 27/3691* (2013.01); *A61L 2300/252* (2013.01); *A61L 2430/34* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 5,993,844 A | * | 11/1999 | Abraham ............... A61K 35/12 424/423 |
| 2007/0244568 A1 | * | 10/2007 | Matsuda ............. A61L 27/3604 623/23.72 |
| 2008/0195229 A1 | | 8/2008 | Quijano et al. |
| 2012/0302499 A1 | * | 11/2012 | Matheny ............. A61L 27/3633 514/8.9 |

FOREIGN PATENT DOCUMENTS

| | | |
|---|---|---|
| CN | 101011604 A | 8/2007 |
| CN | 101366975 A | 2/2009 |
| CN | 101884810 A | 11/2010 |
| CN | 103432627 A | 12/2013 |
| JP | 2012508599 A | 4/2012 |
| WO | 0148153 A1 | 7/2001 |
| WO | 2011132089 A2 | 10/2011 |
| WO | 2012003450 A2 | 1/2012 |
| WO | 2012149253 A1 | 11/2012 |
| WO | 2013009595 A2 | 1/2013 |

OTHER PUBLICATIONS

Sigma "DMEM formulation sheet", available on company webpage at <http://sigma-aldrich.custhelp.com/app/answers/detail/a_id/2292/p/21,706>, last updated Sep. 2, 2015 (Year: 2015).*
International Search Report of PCT/CN2014/078737, dated Sep. 2, 2014.
Anil Srivastava et al, "Use of Porcine Acellular Dermal Matrix as a Dermal Substitute in Rats, Annals of Surgery", Jan. 1, 2001, pp. 400-408.
Ehab Kheir et al: "Development and Characterization of an acellular porcine cartilage bone matrix for use in tissue engineering", Journal of NBiomedical Materials Research Part A, vol. 99A, No. 2, Nov. 19, 2011, pp. 283-294.
Daniel W. Youngstrom et al: "Functional Characterization of Detergent-Decellularized Equine Tendon Extracellular Matrix for Tissue Engineering Applications", Plos One, vol. 8, No. 5, May 27, 2013, p. e64151, XP055350763.
Peter M. Crapo et al: "An overview of tissue and whole organ decellularization processes", Biomaterials, Elsevier Science Publishers BV, Barking, GB, vol. 342, No. 12, Jan. 19, 2011, pp. 3233-3243.
Supplementary European Search Report of EP14840537, dated Mar. 2, 2017.

* cited by examiner

*Primary Examiner* — Emily A Cordas (74) *Attorney, Agent, or Firm* — Banner & Witcoff, Ltd.

(57) ABSTRACT

A method for manufacturing an animal acellular tissue matrix material and a tissue matrix material manufactured by the same. The tissue matrix material manufactured by the method retains an original basic scaffold structure of a tissue extracellular matrix, with an antigen causing immunological rejection in a human body being effectively removed from the animal tissue. An animal dermal matrix manufactured by the method retains the biological integrity of a natural dermal tissue matrix and can be used for restoration and repair of lesion and missing tissues.

13 Claims, 4 Drawing Sheets

METHOD FOR PREPARING AN ANIMAL DECELLULARIZED TISSUE MATRIX MATERIAL AND A DECELLULARIZED TISSUE MATRIX MATERIAL PREPARED THEREBY

TECHNICAL FIELD

The present invention relates to the technical field of treatment of biological tissues and manufacture of tissue matrix materials, and in particular relates to a method for manufacturing an animal acellular tissue matrix material and an acellular tissue matrix material manufactured by the same.

BACKGROUND OF THE RELATED ART

There are great similarity and homology in an extracellular matrix of a tissue and organ of a human body and many animals. A biological matrix material manufactured by decellularization of an allogeneic or xenogenic tissue and organ has been successfully used for the repair and restoration of human tissues in clinical medicine. The decellularized tissue and organ matrix is also widely used for various studies in tissue engineering and regenerative medicine, for example, removing original cell components of a tissue and organ of animals, and re-cellularizing and functionalizing the matrix of the tissue and organ having a three-dimensional tissue scaffold structure by human cells in vitro, thereby finally producing the tissue and organ which can be implanted to human body.

The matrix of the tissue and organ is a three-dimensional scaffold composed of various complex structural proteins and functional proteins, and comprises many other active complexes. Main components include collagenous fiber, glycoprotein, mucoprotein, and the like, and the other components include saccharides such as glycosaminoglycan (hyaluronic acid, chondroitin sulfate), some lipids and growth factors. A good matrix of the tissue and organ has suitable biomechanical strength, and after being implanted into a host, the matrix material provides initial biomechanical support, and regulates cell behavior (e.g., adherence, migration, proliferation and differentiation) by interacting with a host cell, and the matrix of the tissue and organ itself is gradually degraded and converted into a new tissue with the ingrowth of the host cell.

Currently, there are approximately thirty kinds of matrix material products derived from tissues and organs all over the world, which have been used in various clinical medicines such as tissue repair and regeneration. Raw materials of the tissues and organs in these products are derived from tissues of human and various mammals, including blood vessel, cardiac valve, ligament, nerve, skin, small intestinal mucosa, forestomach, pericardium, peritoneum, muscle tendon and bladder, and the like.

A process procedure for manufacturing the matrix of the tissue and organ is very complex, including processes such as collection, preservation, washing, disinfection, decellularization, antigenicity reduction, virus inactivation, and terminal sterilization of the tissue and organ, and the like. There are many existing methods for manufacturing the matrix of the tissue and organ, and they can be classified into a physical method, a chemical method, an enzymatic method and the like according to their action principles of the decellularization. The most commonly used decellularization method is a method in which the physical treatment and chemical treatment are combined. The cellular membrane is damaged by stirring or ultrasonic, mechanical massage or pressurization, freezing and thawing, so that the cell components are released from the cell, further facilitating the subsequent decellularization and washing using a chemical detergent. The physical method itself is generally not sufficient to achieve complete decellularization. Enzymatic treatment method, such as some trypsin, can alter the density and porosity of the tissue extracellular matrix, and cut the connection between the cell surface and the tissue extracellular matrix. In addition, by using different process procedures and methods, the removal efficiency of cells and the effect or damage to the matrix of the tissue and organ are different. In addition to direct damage to the matrix of the tissue and organ, the collection, preservation, washing, disinfection, and decellularization treatment also influence the subsequent processing steps of the tissue and organ. Various treatments will influence and change the biochemical composition of the matrix of the tissue and organ, and the ultrastructure and biomechanical property of the three-dimensional scaffold to different extent, which will influence the response of the host to the implanted matrix material. The evidence of preclinical animal tests and human clinical application demonstrates that there are great differences among various products of the matrix of the tissue and organ in terms of the clinical performance of tissue repair and regeneration. The variation of characteristics of the matrix of the tissue and organ during the manufacture process is one of the main reasons causing the difference of clinical effects of various products.

Content of the Invention

In one aspect, the present invention provides a method for manufacturing an animal acellular tissue matrix material, which comprises the steps of:

(1). collecting a raw material of an animal tissue, wherein the animal tissue is washed to remove blood and other dirt, and cut into a tissue material having a length, a width and a height of the desired specification and dimension, and then the tissue material is preserved at a low temperature;

(2). thawing slowly, and rehydrating the tissue material in a normal saline containing gentamicin;

(3). disinfecting and sterilizing the tissue material in a moderate alkaline solution, wherein the tissue material is then rinsed with sterile pure water, and the pH of the tissue material is adjusted to be neutral;

(4). decellularizing and washing the tissue material;

(5). digesting DNA components of the animal tissue, wherein the animal tissue is then rinsed with a normal saline;

(6). digesting α-Gal antigen of the animal tissue, wherein the animal tissue is then rinsed with a high concentration of a sodium chloride solution, and rinsed with a normal saline;

(7). inactivating the viruses in the animal tissue the animal tissue, wherein the animal tissue is then rinsed with a phosphate buffer solution;

(8). packaging and sealing the animal tissue under an aseptic condition;

(9). terminal sterilization treatment.

In the method, an enzymatic method is used to remove cell components and α-Gal antigen and improve the pliability of a tissue scaffold.

In an embodiment of the present invention, the raw material of the animal tissue in step (1) is selected from skin, dermis, artery, vein, stomach, cartilage, meniscus, small intestine, large intestine, diaphragm, muscle tendon, ligament, nervous tissue, bladder, urethra and ureter.

In an embodiment of the present invention, the washing of the animal tissue to remove blood and dirt in step (1) is performed by using pure water and a physical method or ultrasonic washing.

In a process method for manufacturing the tissue matrix material, the step of preservation of a raw material of a porcine dermis at a low temperature is involved, wherein, the rate of cooling and heating is a very important parameter. If the rate of cooling and heating is too rapid or not uniform within the tissues, tiny cracks can occur in local regions of the tissues and the tissue matrix is prone to be tore when used.

In an embodiment of the present invention, preferably, the tissue material in step (1) is preserved at a temperature of −40° C. or less which is achieved with an average cooling rate of no more than 1.0° C. per minute, and more preferably, the cooling rate is 0.5° C. per minute. The tissue material preserved at a low temperature is slowly thawed in an environment of 5° C. to 12° C. in step (2), to avoid the production of cracks in the tissue due to an over-rapid temperature increase. After the ice is completely melted, the thawed tissue material is rehydrated in a normal saline containing 100 mg of gentamicin per liter for 3 hours to 6 hours in step (2).

In one embodiment of the present invention, the preservation at a low temperature in step (1) is long-term preservation, the method is to lay a porcine dermal material on a piece of protective layer with slightly larger area, such as cotton yarn cloth, paper, plastic film, nylon net or other cloth fabrics, and roll the dermis and the protective layer into one multilayer concentric roll or form a multilayer package form with the dermis and the protective layer being alternated, which is placed into a plastic bag, and kept in a refrigerator at −80° C. or −40° C. for preservation after being sealed.

In the preparation method of embodiments of the present invention, the initial disinfection and sterilization of a raw material of a porcine dermis are involved. The existing methods comprise use of sodium hypochlorite, peroxyacetic acid, hydrogen peroxide, iodine solution, and a high concentration of sodium hydroxide solution (with a pH of 13 or more). After the treatment using these solutions, the tissue matrix is damaged to different extent, especially with the effects of sodium hydroxide, sodium hypochlorite, and iodine solution being greater.

Unlike the disinfection and sterilization technology of the raw material in the existing methods, in an embodiment of the present invention, the moderate alkaline solution in step (3) is a sodium bicarbonate, or sodium hydroxide solution with a pH of 10.5 to 11.5 or an ammonia hydroxide solution with a concentration of 0.1%, the disinfection and sterilization method is to soak the rehydrated tissue material in the moderate alkaline solution for 24 hours to 48 hours with shaking slowly, thereby avoiding the damage of the tissue matrix.

In an embodiment of the present invention, the decellularization method in step (4) is to firstly rinse the disinfected and sterilized and rinsed tissue material in a normal saline containing 2.0 mmol/L of calcium chloride, 2.0 mmol/L of magnesium chloride and 100 mg/L of gentamicin at room temperature for 1 hours to 3 hours, and then add a dispase solution to elute cells.

In one embodiment of the present invention, the dispase solution is a neutral dispase solution, which contains 1 mmol/L to 20 mmol/L of calcium chloride, 1 mmol/L to 20 mmol/L of magnesium chloride and 50 units/L to 400 units/L of dispase, and the method for eluting cells with the dispase solution is to soak the tissue material in the neutral dispase solution, at 37° C. for 24 hours to 36 hours with shaking slowly, and more preferably, the neutral dispase solution contains 2.0 mmol/L of calcium chloride, 2.0 mmol/L of magnesium chloride and 100 units/L to 200 units/L of dispase.

In one embodiment of the present invention, after completing the decellularization in step (4), the washing step is performed. The washing comprises washing with a first detergent and/or washing with a second detergent, wherein the first detergent solution is prepared by dissolving polyethylene glycol tert-octylphenyl ether Triton™ X-100, at a concentration of 0.5%, in a buffer solution of hydroxyethylpiperazine ethane sulfonic acid (pH 7.0~8.0), and the washing method is to soak the tissue material in the first detergent solution at 37° C. for 12 hours to 18 hours with shaking slowly. The second detergent solution is prepared by dissolving sodium deoxycholate, at a concentration of 1.0%, in a phosphate buffer solution (pH 7.2~7.8), and the washing method is to soak the tissue material in the second detergent solution at room temperature for 24 hours to 36 hours with shaking slowly. Meanwhile, other suitable detergents, such as Tween-20, t-octylphenoxyl polyethylene ethoxyethanol and 3-[(3-cholesterol aminopropyl)dimethylamino]-1-propanesulfonic acid, and the like, are used in embodiments of the present invention.

In an embodiment of the present invention, after being soaked in the first detergent solution and the second detergent solution, and prior to step (5), the tissue material is rinsed three times with a buffer solution of 20 mmol/L of hydroxyethylpiperazine ethane sulfonic acid (with a pH between 7.0~8.0) at room temperature, each time for 2 hours to 4 hours.

Due to the existence of DNA of the animal tissues, an inflammatory response is easily caused by the tissue matrix being implanted into a human body. In addition to human and old world monkeys, other mammals all contain α-Gal antigen consisting of glycoprotein or glycolipid with a disaccharide end of α-1,3-galactose residue [Galα(1,3)Gal] in vivo. In particular, the α-Gal antigen in porcine tissues will cause immunological rejection response. One of the methods for eliminating or overcoming the inflammatory response and rejection response is to remove DNA and α-Gal antigen from the animal tissue matrix using specific enzymatic treatment.

In an embodiment of the present invention, the digestion of DNA components of the animal tissue in step (5) is accomplished by adding a deoxyribonuclease solution, wherein the deoxyribonuclease solution is prepared by adding 2.0 mmol/L of calcium chloride, 2.0 mmol/L of magnesium chloride and 5000 enzyme units/L of deoxyribonuclease into a buffer solution of 100 mmol/L of trihydroxymethyl aminomethane-hydrochloric acid with a pH of 7.2, and a method for digesting DNA from the animal tissue is to soak the tissue material in the deoxyribonuclease solution to be treated for 18 hours to 28 hours at 37° C. with shaking slowly, and then place the tissue material in a normal saline to be rinsed twice at room temperature, each time for 1 hours to 3 hours.

In an embodiment of the present invention, digesting α-Gal antigen of the animal tissue in step (6) is accomplished by adding α-galactosidase solution, wherein the formula of the α-galactosidase solution is to add 2.0 mM calcium chloride, 2.0 mM magnesium chloride and 400GALU units of α-galactosidase into per liter of a buffer solution of 10 mM hydroxyethylpiperazine ethane sulfonic acid (with a pH between 7.0~8.0), and a method for digesting the α-Gal antigen of the animal tissue is to soak the tissue material in the α-galactosidase solution, to be washed for 24~36 hours at 37° C. with shaking slowly.

When the tissue matrix implanted into human body is manufactured, it is necessary to remove various residual enzymes. To achieve the above objectives, in an embodiment of the present invention, the washing is performed using a salting-out method, wherein the high concentration of sodium chloride solution in step (6) is a 2 to 5% sodium chloride solution, and a rinsing method is to soak the tissue material in the sodium chloride solution and wash the tissue material twice at room temperature, each time for 2 hours to 4 hours. In one-embodiment, the high concentration of sodium chloride solution can be a 3% sodium chloride solution. Furthermore, the sodium chloride solution can be replaced with other neutral salt solution, such as potassium chloride, magnesium chloride and lithium chloride, and the like.

To increase the safety of the products, in an embodiment of the present invention, said method also relates to a virus inactivation treatment, wherein the virus inactivation agents used in step (7) are hydrogen peroxide and peroxyacetic acid, and a method for the virus inactivation is to soak the tissue material in a solution containing 0.01% to 0.10% hydrogen peroxide, 0.05% to 0.50% acetic acid and 0.05% to 0.50% peroxyacetic acid, to be washed for 2 hours to 3 hours at room temperature with shaking slowly. In another embodiment of the present invention, a solution containing 0.02% hydrogen peroxide, 0.15% acetic acid and 0.10% peroxyacetic acid is used for virus inactivation, with the number of viruses being decreased by $10^6$ or more during 2 hours to 3 hours. The concentration of hydrogen peroxide, acetic acid and peroxyacetic acid may be varied with the number of bacteria.

In an embodiment of the present invention, after the virus inactivation in step (7), the tissue material is rinsed three times at room temperature with a neutral phosphate buffer solution, each time for 2 hours to 4 hours, to remove the residual hydrogen peroxide, acetic acid and peroxyacetic acid.

The terminal sterilization treatment of the tissue product is often one of the most destructive steps for the tissue material. For this reason, in an embodiment of the present invention, a low temperature irradiation is used to perform the treatment in step (9). In another embodiment of the present invention, under the condition of −40° C., the terminal sterilization treatment of the tissue material is performed using 10 kGy to 50 kGy gamma ray, which greatly reduces the damage to the tissue material. In some embodiments of the present invention, a radiation dosage is varied depending on the number of bacteria in the tissue matrix. In another embodiment, the terminal sterilization treatment of the tissue material is performed using 20 kGy to 30 kGy gamma ray.

In some alternative embodiments of the present invention, in addition to the irradiation terminal sterilization method, the tissue matrix in said method can also be sterilized by using ethylene oxide gas after being lyophilized.

In some embodiments of the present invention, the sequence of step (4) (decellularization with enzyme), step (5) (digesting DNA with enzyme) and step (6) (digesting α-1,3-galactose residue antigen with enzyme) can be adjusted or altered as actually required. For example, firstly, α-1,3-galactose residue antigen in animal tissues may be digested, and then the animal tissues are decellularized and the DNA components of animals are digested; or firstly, the animal DNA is eliminated, and then the α-1,3-galactose residue antigen is eliminated and finally treated by decellularization.

Furthermore, in some alternative embodiments of the present invention, if the animals improved by genetic engineering and free of α-Gal antigen are selected, step (6) is omitted and step (7) is directly performed. Meanwhile, to reduce the disadvantageous effect on the proteolysis of the extracellular matrix, the concentration of the dispase, temperature and time will be monitored and optimized while treating. In the process procedure, the specific enzyme inhibitor can further be added, for example, ethylenediamine tetraacetic acid, for inhibiting the activity of the dispase.

Another aspect of the present invention further relates to an animal acellular tissue matrix material manufactured by the above method of the embodiments of the present invention.

In one embodiment of the present invention, said animal acellular tissue matrix material is obtained by using dermis with basement membrane or dermis with basement membrane removed as a raw material of an animal tissue.

In the method for manufacturing an acellular tissue matrix material according to the embodiments of the present invention, a series of steps of treating animal skin tissues and manufacturing the matrix of the tissue and organ as well as a plurality of biochemical solutions and formulas thereof are involved. The dermal tissue matrix material manufactured by the above steps and solutions retains the original basic scaffold structure of the tissue extracellular matrix, main biochemical components and biomechanical strength, with an antigen causing immunological rejection response in the human body being effectively removed from the animal tissue; and improves the flexibility, drapability and the integration performance of wound curved surface of the tissue matrix, and the manufactured animal dermis matrix is similar with human skin, which will not cause the collagen in the tissue matrix to crosslink with other proteins, and will not cause degradation or denaturation, and the decellularized dermis tissue retains the biological integrity of the natural dermal tissue matrix.

DESCRIPTION OF THE DRAWINGS

A: a HE staining section of a fresh porcine dermis.

B: a HE staining section of a dermal matrix after being treated.

C: an immunochemical staining section of α-1,3-galactose residue antigen of the fresh porcine dermis.

D: an immunochemical staining section of α-1,3-galactose residue antigen of the treated dermal matrix.

A, B, C: an immunochemical staining section of collagen type I.

D, E, F: an immunochemical staining section of collagen type III.

A, D: negative staining.

B, E: positive staining of an untreated fresh porcine dermis.

C, F: treated tissue dermal matrixes.

DETAILED DESCRIPTION OF EMBODIMENTS

The embodiments of the present invention are further illustrated in detail by way of examples hereinafter, and intended to illustrate rather than to limit the present invention. Further, it should be noted by those skilled in the art that several improvements and modifications can be made to the present invention without departing from the principle of the present invention, and these improvements and modifications also fall within the protection scope of the present invention.

Example 1: Manufacture And Performance Detection of an Animal Acellular Tissue Matrix Material 1. Manufacture (1) Collection and Preservation of a Tissue and Organ Fresh porcine hide was collected from a newly slaughtered pig, and temporarily preserved in a refrigerator at 4° C. After the porcine hide was dehaired mechanically, the porcine hide was split into a dermis layer having a thickness of about 1.0 mm, which was cryopreserved at −20° C.

(2) Decellularization

After the dermis was thawed, it was firstly flushed with a normal saline twice, each time for 30 minutes. The flushed porcine dermis was soaked in a saline solution containing 100 mg of gentamicin per liter, and 2.0 millimole concentration of calcium chloride, 2.0 millimole concentration of magnesium chloride, and 150 units per liter of neutral dispase were further added to the solution, and the dermis is treated at 37° C. for 24 hours.

(3) Washing

After being soaked in gentamicin, the dermis was washed with a 0.5% polyethylene glycol tert-octylphenyl ether Triton™ X-100 solution for 16 hours. After decellularization and washing, the dermis was flushed with a normal saline twice, each time for 120 minutes.

(4) Digestion of DNA and Removal of α-1,3-Galactose Residue Antigen

To each liter of the solution were further added 2.0 millimole concentration of calcium chloride, 2.0 millimole concentration of magnesium chloride, 5000 units of deoxyribonuclease and two tablets of Beano from Glaxosmithkline (containing α-galactosidase), and the dermis was treated at room temperature for 20 hours.

(5) Virus Inactivation

After being washed, the dermis was sterilized and virus inactivated with a solution containing 0.02% hydrogen peroxide, 0.15% acetic acid and 0.10% peroxyacetic acid for 2 hours.

(6) Washing and Preservation

Finally, the dermis was flushed with sterile normal saline until no polyethylene glycol tert-octylphenyl ether Triton™ X-100 and enzyme remained. The treated dermal matrix was temporarily preserved in 6% glycerin.

2. Performance Detection

It was indicated by measurements that the tensile strength of the material was 15.0±3.6 megapascal (N=24); the strength of the suture was 56±13 newton (N=24); each 100 g by wet weight of the dermis matrix contained 24.2±2.9 g of a dry matter material of a dermis (N=15).

It was showed by analysis using differential scanning calorimeter that the initial denaturation temperature of the tissue matrix material was 58.0±0.4° C. (N=5), and the value of enthalpy change was 61.6±2.1 Joule per gram by dry weight (N=5), which were not significantly different from the dermis matrix in natural state from the raw material of the dermis.

Figure 1:
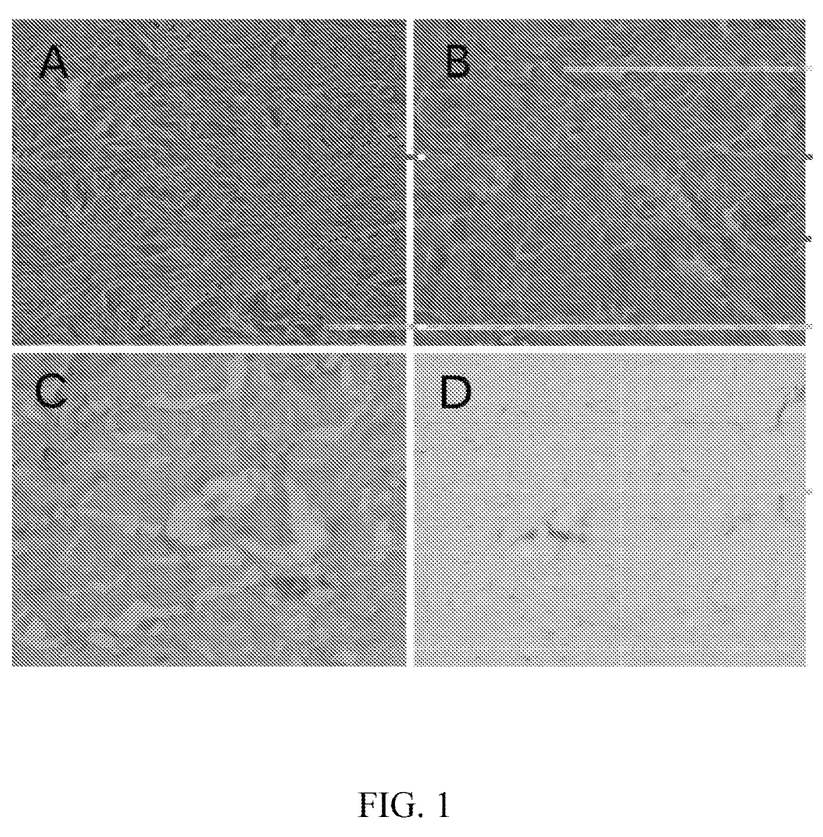
FIG. 1: Histology of tissue sections.
Figure 2:
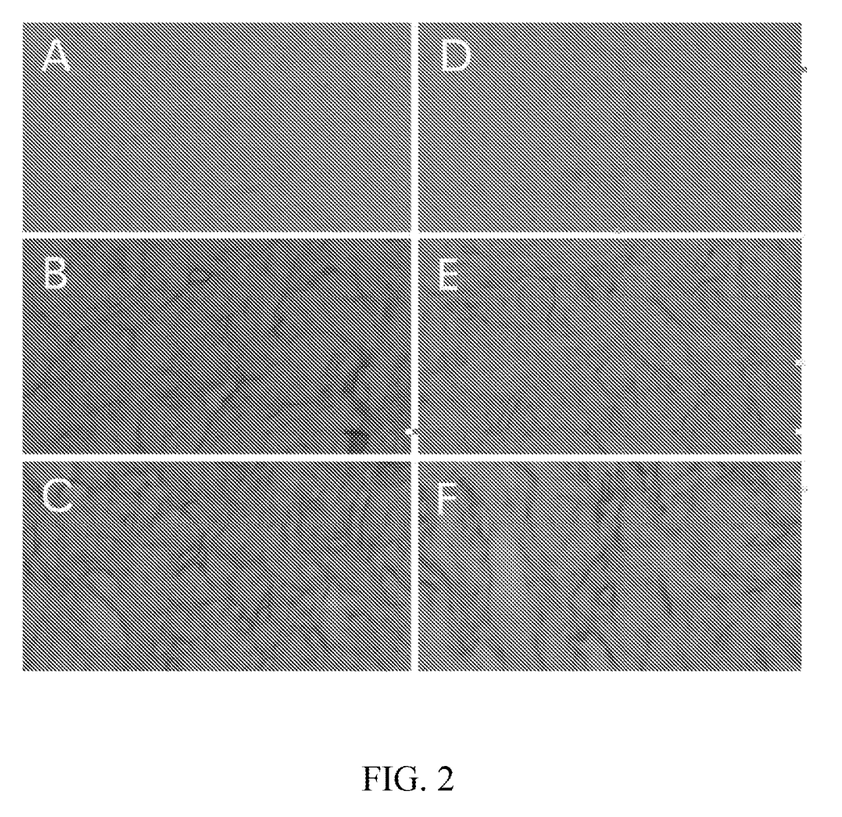
FIG. 2: Histology of tissue sections.

There was no significant change or damage on the characteristics of the dermis matrix in the whole process course. It was indicated by analysis of the tissue section that there were no cell components (e.g., deoxyribonucleic acid DNA) and α-1,3-galactose residue antigen in the matrix, see FIG. 1 for details. It was also showed by immunochemical staining analysis of collagen type I and III that there was no damage on the collagen in the dermis matrix in the treatment process, see FIG. 2 for details.

Example 2: Determination of Appropriate Conditions for Washing and Disinfecting the Dermis Fresh dermis was collected from a porcine body, and the fresh porcine dermis was treated in sodium hydroxide solutions with pH of 10.6, 11.5 and 11.8 at 37° C., respectively. Each kilogram of the porcine hide was in 4 liter of sodium hydroxide solution, with the control of phosphate buffer. After 24 hours, colony-forming unit per milliliter solution was determined. The phosphate buffer contained 10.3±1.3 logarithmic colony-forming unit (Log CFU)(N=3); and the logarithmic colony-forming unit in the solution with pH of 10.6, 11.5 and 11.8 was 2.1±0.1, 0 and 0, respectively. As could be seen, disinfection and sterilization effect in moderate alkaline solution was significant.

It was demonstrated by using differential scanning calorimeter that the tissue matrix was damaged by washing with an alkaline solution with a pH of 11.5 or more, and the stability of protein in the tissue matrix was significantly reduced. The damage of high pH on the tissue matrix further demonstrated the irreversible imbibition and induration of the tissue matrix. This example determined a more suitable condition for washing and disinfecting the dermis, which comprised adjusting pH to be between 10.5~11.5.

Example 3: Manufacture and Performance Detection of an Animal Acellular Tissue Matrix Material 1. Manufacture (1) Collection and Preservation of a Tissue and Organ Fresh porcine hide was collected from a newly slaughtered pig, and temporarily preserved in a refrigerator at 4° C. After the porcine hide was dehaired mechanically, the porcine hide was split into a dermis layer having a thickness of about 1.0 mm.

(2) Collection and Washing

After collection and washing (see example 1), the porcine dermis with a thickness of 1.0 mm was temporarily preserved in a refrigerator at −80° C.

(3) Decellularization

After being thawed, the dermis was flushed with 5 mmol/L of hydroxyethylpiperazine ethane sulfonic acid solution (pH 7.4), and was then treated at 37° C. for 18 hours after adding 2.0 mmol/L of calcium chloride and 0.2 unit per milliliter of neutral dispase.

(4) Washing

The dermis was washed with 1.0% sodium deoxycholate solution at 37° C. for 20 hours.

(5) Digestion of DNA and α-1,3-Galactose Residue Antigen

After the dermis was flushed with sterile normal saline for 120 minutes, to each liter of the solution were further added 2.0 mM of calcium chloride, 2.0 mM of magnesium chloride, 4000 units of recombinant deoxyribonuclease and 200 GALU units of α-galactosidase extracted from seeds of green coffee bean, and the dermis was treated at 37° C. for 24 hours.

(6) Virus Inactivation

After being washed with sterile normal saline, the dermis was sterilized with 0.05% hydrogen peroxide, 0.30% acetic acid and 0.20% peroxyacetic acid for 2 hours.

(7) Washing

The dermis was flushed with a sterile normal saline until no sodium deoxycholate, recombinant deoxyribonuclease and α-galactosidase was remained.

(8) Terminal Sterilization Treatment

The treated dermal matrix was preserved in sterile normal saline solution containing 12% glycerin, and sterilized by 25 kGy of gamma ray.

2. Performance Detection

It was demonstrated by measurement using the durometer with OO-type probe that the softness of the untreated porcine dermis was 40±8.6 (N=24), the softness of the acellular porcine dermis was 13.0±4.0 (N=25), and the softness of human dermis was 14.2±6.1 (N=40). It was demonstrated that there was no statistically significant difference in the softness between the porcine dermal matrix after decellularization treatment and the human dermis tissue, as compared to the untreated porcine dermis (much harder). Further, it was demonstrated that the method of the examples of the present invention improved the flexibility, drapability and the integration performance of wound curved surface of the tissue matrix.

It was demonstrated by analysis of the tissue section that α-1,3-galactose residue antigen of the produced tissue matrix was removed completely, the result of staining was negative, and no antigen was expressed. DNA content was determined by using a QuantiT-PicoGreen fluorochrome method, the results of which indicated that each gram of the fresh porcine dermis contained about 84.0±10.2 microgram of DNA (N=3), each gram of the porcine dermis after being washed and disinfected contained 62.9±9.5 microgram of DNA (N=3), each gram of the tissue matrix after being treated by decellularization and washed only contained 1.9±1.1 microgram of DNA (N=3), and the animal DNA content was averagely reduced by 97.7%. It was showed by analysis using differential scanning calorimeter that the initial denaturation temperature of the tissue matrix material was 54.7±0.2° C. (N=3), the value of enthalpy change was 59.5±3.1 Joule per gram by dry weight (N=3). As compared with the dermis in natural state from the raw material of the porcine dermis, the initial denaturation temperature was only reduced by 3.3° C., and there was no significant difference in the value of enthalpy change, which illustrated that there was no significant change or damage on the characteristics of the tissue matrix in the whole manufacture process (including terminal radiation sterilization by gamma ray).

The content of collagen in the tissue matrix was determined by hydroxyproline method, and the tissue matrix of porcine hide after terminal radiation sterilization by gamma ray contained 91.0±3.0% (N=6) of collagen. The content of elastin was determined by Fastin staining method, and the tissue matrix after terminal radiation sterilization by gamma ray contained 0.92±0.21% (N=6) of elastin, which was reduced by 71.4% as compared with the untreated porcine dermal material.

Figure 3:
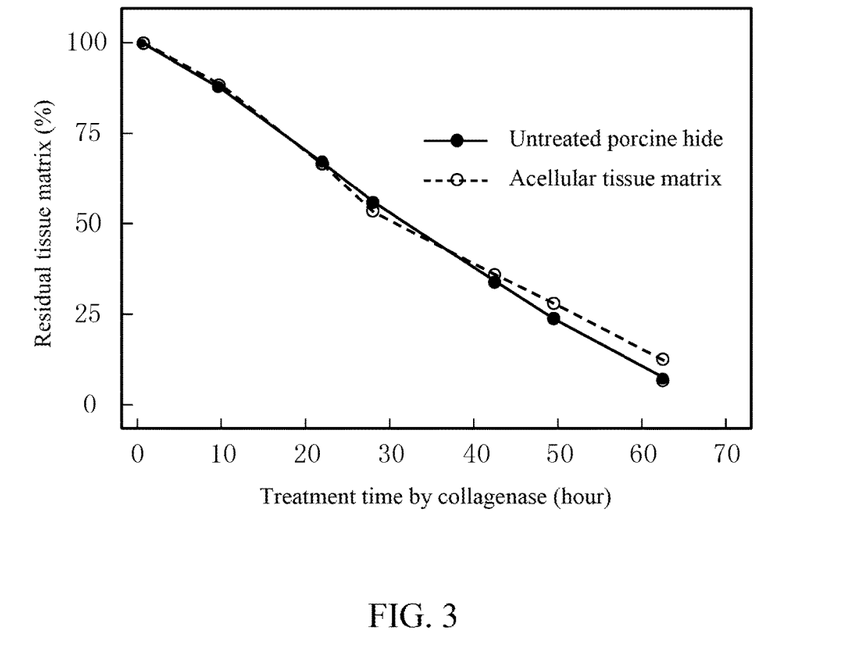
FIG. 3: A characteristic diagram of an acellular tissue matrix material against the hydrolysis via collagenase after the terminal sterilization by gamma ray irradiation.

Characteristics of the acellular tissue matrix material against hydrolysis via collagenase may be used to study the stability of collagen in the acellular tissue matrix material manufactured by the examples of the present invention after terminal radiation sterilization by gamma ray. The manufactured acellular tissue matrix material was placed into a trihydroxymethyl aminomethane-hydrochloric acid solution containing κ units of collagenase per milliliter (10 mM, pH 7.5), and incubated at 37° C. for up to 64 hours. The results showed that as compared with the untreated porcine dermal material, characteristics of the acellular tissue matrix manufactured by the method of the examples of the present invention against hydrolysis via collagenase did not change after terminal radiation sterilization by gamma ray, see FIG. 3 for details.

Figure 4:
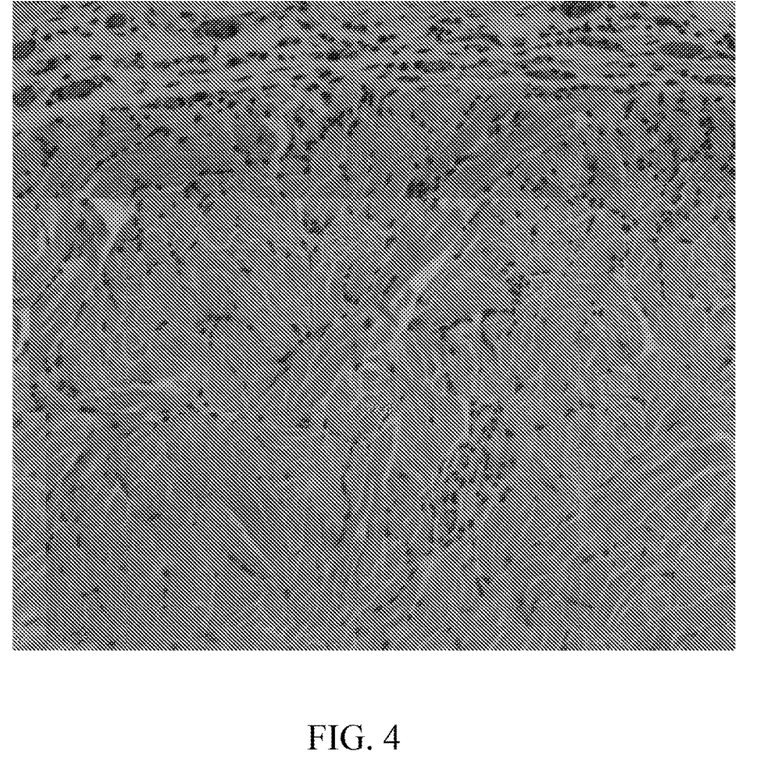
FIG. 4: An HE staining histology showing host cell ingrowth and neovascularization, after two weeks from the subcutaneous implantation of an acellular tissue matrix material into a rat.

By utilizing recellularization characteristics of the acellular tissue matrix material manufactured by the method of the examples of the present invention, an animal evaluation experiment was performed with rats (*Rattus norvegicus* Lewis). After 8 rats were narcotized, the hair on the back was removed off by an electrical shaver, the surgical site was scrubbed with 70% alcohol, and a separate incision was cut on the upper and lower and left and right back, to form a small pocket, the size of which was suitable to accommodate 1×1 cm of sample (~about 1 mm thick). The acellular tissue matrix material sample was subcutaneously implanted into the rat. After the surgery, if the rats showed signs of pain, a buprenorphine solution (0.05 mg/kg) was used to stop pain. The rats were sacrificed after two weeks, and the implanted acellular tissue matrix material was taken out and fixed with a 10% neutral formalin solution. Host cell ingrowth and angiogenesis of rats were observed by a tissue section method. The results demonstrated that a large number of host cells were grown into the tissue matrix material within two weeks, and the neovascularization began, with no adverse reaction being observed, see FIG. 4 for details.

What we claim is:

1. A method for manufacturing an animal acellular tissue matrix material, comprising the steps of:
   (1) collecting a raw material of an animal tissue, wherein the animal tissue is washed to remove blood and dirt, and cut into a tissue material having a length, a width and a height of the desired specification and dimension, and then the tissue material is preserved at a low temperature below freezing;
   (2) thawing slowly, and rehydrating the tissue material from step (1) in normal saline containing gentamicin;
   (3) disinfecting and sterilizing the tissue material from step (2) in a moderate alkaline solution, then rinsing the tissue material with sterile pure water, and adjusting the pH of the tissue material to be neutral, wherein the moderate alkaline solution is a sodium bicarbonate or sodium hydroxide solution with a pH of 10.5 to 11.5 or an ammonia hydroxide solution with a concentration of 0.1%, wherein in the step of disinfection and sterilization, the rehydrated tissue material is soaked in the moderate alkaline solution for 24 hours to 48 hours with slow shaking;
   (4) decellularizing and washing the tissue material from step (3),
   wherein the decellularizing comprises rinsing the disinfected, sterilized and rinsed tissue material in normal saline containing 2.0 mmol/L of calcium chloride, 2.0 mmol/L of magnesium chloride and 100 mg/L of gentamicin at room temperature for 1~3 hours, and then adding a dispase solution to remove the cells, wherein the dispase solution is a neutral dispase solution containing 1 mmol/L to 20 mmol/L of calcium chloride, 1 mmol/L to 20 mmol/L of magnesium chloride and 50 units/L to 400 units/L of dispase, and the tissue material is soaked in the neutral dispase solution at 37° C. for 24 hours to 36 hours with slow shaking;

wherein the washing comprises washing with a first detergent solution at 37° C. for 12 hours to 18 hours with slow shaking and washing with a second detergent solution at room temperature for 24 hours to 36 hours with slow shaking, wherein the first detergent solution is prepared by dissolving polyethylene glycol tert-octylphenyl ether, at a concentration of 0.5%, in a buffer solution of hydroxyethylpiperazine ethane sulfonic acid with a pH between 7.0 and 8.0; and the second detergent solution is prepared by dissolving sodium deoxycholate, at a concentration of 1.0%, in phosphate buffer solution with a pH between 7.2 and 7.8;

(5) digesting DNA components of the animal tissue, wherein the animal tissue is then rinsed with normal saline;

(6) digesting α-Gal antigen of the animal tissue, wherein the animal tissue is then rinsed with a 2% to 5% high concentration sodium chloride solution, and then rinsed with normal saline, and when the raw material of the animal tissue has been improved by genetic engineering to have no α-Gal antigen is selected, step (6) is omitted and step (7) is directly performed;

(7) inactivating any viruses in the tissue material and then rinsing the tissue material;

(8) packaging and sealing the tissue material under an aseptic condition; and (9) terminal sterilization treatment of the tissue material to obtain the animal acellular tissue matrix material;

wherein an enzymatic method is used to remove cell components and α-Gal antigen and improve the flexibility of a scaffold.

2. The method according to claim 1 wherein, the washing of the animal tissue to remove blood and dirt in step (1) is performed by using pure water and a physical method or an ultrasonic method, or wherein the tissue material obtained in step (1) is preserved at a temperature of −40° C. or less which is achieved with a cooling rate of no more than 1.0° C. per minute or the cooling rate is 0.5° C. per minute.

3. The method according to claim 1, wherein the preservation at a low temperature in step (1) is long-term; the tissue material is placed on a piece of protective layer of cotton yarn cloth, paper, plastic film, nylon net or a suitable cloth fabric with an area larger than that of the tissue material, and roll the tissue material and the protective layer into one multilayer concentric roll or form a multilayer package form with the tissue material and the protective layer being alternated; the multilayer concentric roll or the multilayer package form is placed into a bag; and cryopreserved at −80° C. to −40° C. after being sealed.

4. The method according to claim 1, wherein the tissue material preserved at a low temperature is thawed slowly in an environment of 5° C. to 12° C. in step (2), or wherein the thawed tissue material is rehydrated in a normal saline containing 100 mg of gentamicin per liter in step (2).

5. The method according to claim 1 wherein the neutral dispase solution contains 2.0 mmol/L of calcium chloride, 2.0 mmol/L of magnesium chloride and 100 units/L to 200 units/L of dispase.

6. The method according to claim 1 wherein after being soaked in the first detergent solution and the second detergent solution, and prior to step (5), the tissue material is rinsed three times with a buffer solution of 20 mmol/L of hydroxyethylpiperazine ethane sulfonic acid with a pH between 7.0 and 8.0 at room temperature, each time for 2 hours to 4 hours.

7. The method according to claim 1, wherein digesting DNA components of the animal tissue in step (5) is accomplished by soaking the tissue material in a deoxyribonuclease solution for 18 hours to 28 hours with slow shaking, and then rinsing the tissue material twice in normal saline at room temperature, each time for 1 hours to 3 hours, wherein the deoxyribonuclease solution is prepared by adding 2.0 mmol/L of calcium chloride, 2.0 mmol/L of magnesium chloride and 5000 enzyme units/L of deoxyribonuclease into a buffer solution of 100 mmol/L of tri-hydroxymethyl aminomethane-hydrochloric acid with a pH of 7.2.

8. The method according to claim 1, wherein digesting α-Gal antigen of the animal tissue in step (6) is accomplished by soaking the tissue material in an α-galactosidase solution and then washing the tissue for 24 hours to 36 hours with slow shaking, wherein the α-galactosidase solution is prepared by adding 2.0 mmol/L of calcium chloride, 2.0 mmol/L of magnesium chloride and an amount of 400GALU units/L of α-galactosidase into a buffer solution of 10 mmol/L of hydroxyethylpiperazine ethane sulfonic acid with a pH between 7.0 and 8.0.

9. The method according to claim 1, wherein the rinsing step of step (6) is to soak the tissue material in a 3% high concentration sodium chloride solution and wash the tissue material twice at room temperature, each time for 2 hours to 4 hours.

10. The method according to claim 1 wherein agents used in the virus inactivation in step (7) are hydrogen peroxide and peroxyacetic acid, and in the step of the virus inactivation, the tissue material is soaked in a solution containing 0.01% to 0.10% hydrogen peroxide, 0.05% to 0.50% acetic acid and 0.05% to 0.50% peroxyacetic acid, and then is washed for 2 hours to 3 hours at room temperature with slow shaking.

11. The method according to claim 1, wherein after the virus inactivation in step (7), the tissue material is rinsed three times at room temperature with a neutral phosphate buffer solution, each time for 2 hours to 4 hours.

12. The method according to claim 1, wherein the terminal sterilization treatment in step (9) is to perform the sterilization treatment by using low temperature gamma ray irradiation or ethylene oxide gas, with the treatment dosage of gamma ray being 10 kGy to 50 kGy.

13. The method according to claim 1, wherein the sequence of step (4), step (5) and step (6) can be adjusted as required.

* * * * *